(12) United States Patent
Becker et al.

(10) Patent No.: US 7,803,301 B2
(45) Date of Patent: Sep. 28, 2010

(54) PROCESS FOR MAKING A MOLDED VALVE HOUSING FOR A PROSTHESIS OR AN ORTHOSIS

(75) Inventors: Karl Becker, Duderstadt (DE); Klaus-Peter Anhalt, Rhumspringe (DE)

(73) Assignee: Otto Bock HealthCare IP GmbH & Co. KG, Duderstadt (DE)

( * ) Notice: Subject to any disclaimer, the term of this patent is extended or adjusted under 35 U.S.C. 154(b) by 514 days.

(21) Appl. No.: 11/746,226

(22) Filed: May 9, 2007

(65) Prior Publication Data
US 2007/0276510 A1    Nov. 29, 2007

(30) Foreign Application Priority Data
May 9, 2006    (DE) .................. 10 2006 021 857

(51) Int. Cl.
| | |
|---|---|
| *B27N 3/10* | (2006.01) |
| *B29C 45/14* | (2006.01) |
| *B28B 7/22* | (2006.01) |
| *B28B 5/02* | (2006.01) |
| *B29B 13/00* | (2006.01) |
| *A61F 2/60* | (2006.01) |

(52) U.S. Cl. .................. 264/257; 264/255; 264/294; 264/271.1; 623/33

(58) Field of Classification Search .............. 623/33
See application file for complete search history.

(56) References Cited

U.S. PATENT DOCUMENTS

| | | | | |
|---|---|---|---|---|
| 1,153,532 A | * | 9/1915 | Apgar .................. | 12/146 M |
| 1,693,091 A | * | 11/1928 | Loth .................. | 623/33 |
| 1,907,511 A | * | 5/1933 | Davies .................. | 623/33 |
| 2,689,351 A | * | 9/1954 | Schindler .................. | 12/146 M |

(Continued)

FOREIGN PATENT DOCUMENTS

AT    369978    11/1979

(Continued)

OTHER PUBLICATIONS

EP Search Report mailed Aug. 20, 2007, 6 pgs.

*Primary Examiner*—Christina Johnson
*Assistant Examiner*—Benjamin Schiffman
(74) *Attorney, Agent, or Firm*—Faegre & Benson LLP

(57) ABSTRACT

A process is provided for casting a mounting which is attachable to a human body and which takes the form of a prosthesis socket or of an orthosis part. The mounting includes a reinforcement in the shape of a grid or frame located in the core region of the mounting and is surrounded by a lower polyurethane sublayer and a superposed polyurethane sublayer. The process includes a) providing a first spacer material to be soaked with a incompletely reacted polyurethane, b) producing a reinforcement thereon, c) removing the reinforcement, d) casting the lower polyurethane sublayer by saturating the first spacer material with the incompletely reacted polyurethane, e) superimposing the reinforcement on the polyurethane surface of the lower polyurethane, f) applying a second spacer material to be soaked with a partially reacted polyurethane and g) casting the superposed polyurethane sublayer by saturating the second spacer material with the incompletely reacted polyurethane. The first spacer material is positioned at the lower polyurethane sublayer. The second spacer material takes the form of the superposed polyurethane sublayer. The polyurethane sublayers come into contact and both sublayers bond reactively and enclose the reinforcement.

38 Claims, 2 Drawing Sheets

U.S. PATENT DOCUMENTS

| | | | |
|---|---|---|---|
| 3,545,046 A * | 12/1970 | Colley | 24/68 T |
| 3,954,931 A | 5/1976 | Helmuth et al. | |
| 4,635,626 A | 1/1987 | Lerman | |
| 5,156,631 A | 10/1992 | Merlette | |
| 5,246,464 A * | 9/1993 | Sabolich | 623/33 |
| 5,258,036 A * | 11/1993 | Edenbaum et al. | 623/33 |
| 5,263,990 A | 11/1993 | Handal | |
| 5,312,669 A * | 5/1994 | Bedard | 428/105 |
| 5,571,208 A * | 11/1996 | Caspers | 623/32 |
| 5,718,925 A * | 2/1998 | Kristinsson et al. | 425/2 |
| 5,728,170 A * | 3/1998 | Becker et al. | 623/37 |
| 5,755,812 A * | 5/1998 | Becker et al. | 623/33 |
| 5,885,509 A * | 3/1999 | Kristinsson | 264/314 |
| 5,888,231 A * | 3/1999 | Sandvig et al. | 623/36 |
| 5,971,729 A * | 10/1999 | Kristinsson et al. | 425/2 |
| 5,972,036 A * | 10/1999 | Kristinsson et al. | 623/33 |
| 6,156,071 A * | 12/2000 | Biedermann et al. | 623/33 |
| 6,991,444 B1 * | 1/2006 | Laghi | 425/2 |
| 2005/0149202 A1 | 7/2005 | Schaffer et al. | |
| 2008/0004715 A1 * | 1/2008 | Asgeirsson | 623/33 |

FOREIGN PATENT DOCUMENTS

| | | |
|---|---|---|
| DE | 1143633 | 12/1957 |
| JP | 06285101 A * | 10/1994 |
| JP | 09098995 A * | 4/1997 |
| WO | 03/034904 A2 | 5/2003 |

* cited by examiner

PROCESS FOR MAKING A MOLDED VALVE HOUSING FOR A PROSTHESIS OR AN ORTHOSIS

BACKGROUND OF THE INVENTION

The invention relates to a process for casting a mounting which is to be attached to a human body and which takes the form of a prosthesis socket or of an orthosis part with internal reinforcement in the shape of a grid or frame.

A prosthesis is an artificial replacement for an amputated limb that is secured to the remainder of the limb and specifically and particularly to the amputated limb. To this end, the prosthesis has a receptacle in the shape of a funnel or cup for the amputated limb, hereinafter termed "prosthesis socket". Ideally, the prosthetic socket is intended to precisely fit the amputated limb and to an produce a transfer of force from the amputee's body to the prosthesis with no significant areas generating pressure or chafing. If possible, the socket should be capable of elastic adaptation to small dimensional changes of the limb (for example, when the amputated limb swells and reverts to normal size after swelling).

There are similar requirements placed upon what are known as orthoses or those retaining parts which are close to the body. Orthoses are devices which externally hold and support the body or limbs of the body, often being termed braces or splints.

In order to meet the requirements, sockets and other orthopaedic holders (orthoses) that directly contact the body are generally manufactured from plastics which while strong and dimensionally stable, have at least some regions of elasticity or softness and pliability.

To this end, it is common to combine various plastics in a plurality of layers, and within plastic layers, to provide reinforcement, composed of, e.g., woven or knitted materials or of carbon fibers (generally in the form of carbon-fiber mats). It is also possible that the reinforcement is used specifically in certain zones of the mounting component, or that certain, e.g. particularly soft, materials in the manner of an adhesive plaster (cushioning, patches) are substituted for the main material in selected regions or are included in addition to the main material.

Techniques used to construct laminates with polymer-saturated textile reinforcement include winding or casting. These are industrial processes known to orthopaedic technologists. The winding technique winds bandages saturated with an incompletely reacted polymer onto a form, or if appropriate, directly onto the limb stump. The wound capsule is then permitted to harden. As an alternative, saturated textile stockings can be applied in one or more layers to a form. This technique is also often used for structures composed of plaster of Paris, including models made from plaster of Paris (positive cast replica, negative cast replica).

The casting technique casts an incompletely hardened or reacted liquid polymer into a suitable socket cavity or mounting cavity which can be formed from the male mold of the limb stump and a female mold obtained with the aid of a spacer medium over the male mold. The spacer medium is either removed prior to casting (e.g., unfilled mold casting) or, in the case of a porous spacer medium, can be incorporated concomitantly, i.e. incorporated in the casting, so that a filled or reinforced component is produced. In particular, the spacer medium can be a porous filler (e.g., hardened foam or solid granules) or can be composed of textile layers or other layers that absorb liquid (e.g., wound bandages, stocking, socks and textile sublayers in general). A suction technique is often used to facilitate casting into narrow hollow molds. While the liquid and generally viscous polymer precursor (e.g., prepolymers or mixture of starting materials) is cast or injected into the hollow mold, air is sucked out from the same space (generally at another point by way of a valve) in order to facilitate the inflow of the liquid.

Very high-viscosity materials which cannot be cast are often spread onto a male mold, textile sublayers or reinforcement sublayers situated thereover.

EP 201 884 A1 discloses a process for producing a prosthesis with a socket in which a conventional winding-casting technique is used that includes cushioning composed of a viscoelastic material. The socket is composed of the saturated winding bandages and is relatively stiff. While the cushioning can mitigate pressure points, it does not have the necessary elasticity for ideal transmission of pressure- and shear-derived forces.

EP 650 708 B1 discloses a multiple-stage process for producing a socket and a lining. The process is intended inter alia to ensure full contact between the socket and the amputated stump and to increase the transmission of impact- and shear-derived forces. The soft elastic lining is composed of a viscoelastic polyurethane which is produced from an aromatic diisocyanate and elasticizing polyols. The two-part structure composed of the socket and the lining individually and extensibly molded on the amputated stump is troublesome for the user to apply and is often perceived as constricting. The lining does not remove the additional need for the socket to be designed in a relatively complex manner with regions of varying stiffness, elasticity and softness to increase comfort.

There are also known sockets composed of polyurethane which are dimensionally stable but which have the softness and elasticity to reversibly deform under pressure, with interior reinforcement in the form of a relatively stiff frame or grid. By way of example, a carbon-fiber-reinforced windowed polyacrylate layer forms the frame. A disadvantage found with these sockets manufactured from a plurality of individual layers is that the layers can separate from one another, in particular at the edges, making the sockets unusable over time.

BRIEF SUMMARY OF THE INVENTION

It is therefore an object of the invention to design a socket whose regions are composed of different materials and in which a polyurethane surrounds a reinforcement, and to provide a suitable process for its production in such a way as to eliminate the separation of individual layers from one another.

In order to achieve this object, a process applies over the shape of an amputated stump, in succession, a first polyurethane sublayer which comprises a polyurethane (PU) that can be processed by casting, a reinforcement, and a further polyurethane sublayer The process is characterized by the particular procedure of steps a) to g) described below.

In a first aspect, the invention is a process for casting a mounting which is attachable to a human body and which takes the form of a prosthesis socket or of an orthosis part. The mounting includes a reinforcement in the shape of a grid or frame located in the core region of the mounting and is surrounded by a lower polyurethane sublayer and a superposed polyurethane sublayer. The process includes a) providing a first spacer material in spatial relation to the desired lower polyurethane sublayer, b) forming a reinforcement on the first spacer material, c) removing the reinforcement, d) casting the lower polyurethane sublayer by saturating the first spacer material with an incompletely reacted polyurethane material, e) superimposing the reinforcement on a surface of the lower polyurethane sublayer, f) applying a second spacer material and g) casting the superposed polyurethane sublayer by saturating the second spacer material with an incompletely reacted polyurethane material. The second spacer material takes the form of the superposed polyurethane sublayer. The polyurethane sublayers come into contact and both sublayers bond reactively and enclose the reinforcement.

In a second aspect, the invention is a process for casting a mounting attachable to a human body and which takes the form of a prosthesis socket having a grid-shaped reinforcement at its core region The process includes a) providing a first spacer material in spatial relation to a desired first polyurethane sublayer, b) producing the reinforcement in the shape of a grid on the first spacer material, c) removing the reinforcement, d) casting the first polyurethane sublayer by saturating the first spacer material with an incompletely reacted polyurethane material, e) superimposing the reinforcement on a free polyurethane surface of the first polyurethane sublayer prior to complete reaction of the polyurethane material, f) applying a second spacer material, and g) casting a second polyurethane sublayer by saturating the second spacer material with an incompletely reacted polyurethane material so that the first and second polyurethane sublayers bond reactively via a simultaneous shared hardening process and enclose the reinforcement where the first and second polyurethane sublayers come into contact.

In a third aspect the invention is a process for casting a prosthesis socket having an inner polyurethane sublayer, an outer polyurethane sublayer and a reinforcement positioned between the inner and outer polyurethane sublayers. The process includes a) providing a first spacer material in spatial relation to the desired inner polyurethane sublayer, b) producing the reinforcement having a grid or frame shape on the first spacer material, c) removing the reinforcement, d) casting the inner polyurethane sublayer by saturating the first spacer material with an incompletely reacted polyurethane material, e) superimposing the reinforcement on a polyurethane surface of the inner polyurethane sublayer in a state of polymerization after achievement of dimensional stability, f) applying a primer at least on an edge region of the inner polyurethane sublayer and outside an area on which the reinforcement lies, g) applying a second spacer material and h) casting the outer polyurethane sublayer by saturating the second spacer material with an incompletely reacted polyurethane material. The primer aids the reactive bonding between the inner and outer polyurethane sublayers when the inner polyurethane sublayer has hardened such that the inner and outer polyurethane sublayers enclose the reinforcement where the inner and outer polyurethane sublayers come into contact.

In a fourth aspect, the invention is a mounting attachable to a human body. The mounting includes a core region, a grid- or frame-like reinforcement in the core region having perforations and a uniform, fully reacted region formed of a casting resin surrounding the reinforcement and penetrating the perforations of the reinforcement. The reinforcement has a stiffness higher than its immediate surroundings and the reacted region has a stiffness lower than the reinforcement.

DETAILED DESCRIPTION OF THE INVENTION

Figure 1A:
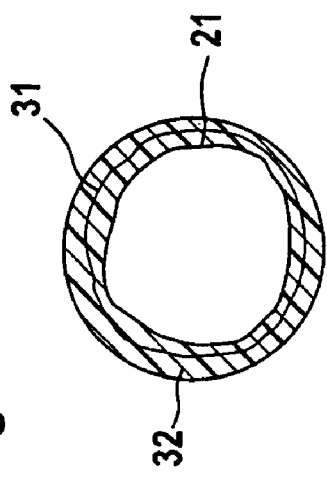
FIG. 1a is a cross-sectional view of a prosthesis socket during a first process stage.

A process is provided for casting a mounting which is attachable to a human body and which takes the form of a prosthesis socket or of an orthosis part. The mounting has a grid- or frame-shaped reinforcement located in its core region and has the following fundamental layer structure: a first (lower) polyurethane (PU) sublayer, a reinforcement in the core region and a second (superposed) polyurethane (PU) sublayer.

A first embodiment of the method includes the following steps in the stated sequence:

a) providing a spacer material which can be soaked with an incompletely reacted polyurethane in the form of a limb-proximal sub-layer;

b) producing a reinforcement in the shape of a grid or frame around the spacer material or shelling over the spacer material, c) removing the reinforcement, d) casting the first polyurethane sublayer by saturating the spacer material with the incompletely reacted polyurethane, e) superimposing the reinforcement on the polyurethane surface of the first polyurethane sublayer in a state of polymerization after dimensional stability is achieved, f) applying a second spacer material which can be soaked with an incompletely reacted polyurethane which takes the form of a desired second PU sublayer, and g) casting the second PU sublayer by saturating the second spacer material with the incompletely reacted polyurethane so that the first and second PU sublayers come into contact and both sublayers bond reactively and enclose the reinforcement.

The spacer material takes the form of a desired limb proximal the first PU sublayer. The first and second PU sublayers bond with the aid of a primer applied between the PU sublayers and/or via a shared hardening process of the two PU sublayers.

The PU casting resin is provided as a multi-component system where the components are mixed immediately prior to use, i.e. casting or saturation of the spacer material. One of these components preferably comprises a prepolymer of at least one isocyanate, and in particular aliphatic isocyanates or predominantly aliphatic isocyanates.

The raw materials for the polyurethane composition are selected so that the composition has good casting properties and exhibits setting behavior such that the composition is not completely polymerized for a period of at least about one to about two hours after the composition has achieved dimensional stability. The selection takes place through preliminary experiments within the scope of the principles stated above. The composition can be a colored composition, for example skin-toned colors as known in principle in the art.

Due to the setting behavior of the casting resin, the complexity of the structure of the mounting and other applicationspecific requirements, various versions or embodiments of the method of processing a mounting can be particularly advantageous.

According to a second embodiment of the invention, steps a) to d) are carried out as described above and steps e) to g) are carried out in the following manner:

e) superimposing the reinforcement on the free polyurethane surface of the first PU sublayer in a state of polymerization after dimensional stability has been achieved and before the reaction has been completed, f) applying a second spacer material, which can be soaked with a partially reacted polyurethane and which takes the form of a desired second PU sublayer, and g) casting the second PU sublayer by saturating the second spacer material so that the two PU sublayers bond reactively via a simultaneous shared hardening and enclose the reinforcement where the two PU sublayers come into contact during hardening of the polyurethane.

The second embodiment described above is particularly advantageous for slow-hardening casting resins or when particularly rapid operation is technically possible.

According to a third embodiment of the invention, steps a) to d) are again executed as stated above in the first embodiment and steps e) to g) are executed as stated below:

e) superimposing the reinforcement on the polyurethane surface of the first PU sublayer in a state of polymerization after dimensional stability has been achieved and a primer has been applied at least on the edge region of the first PU sublayer outside the area on which the reinforcement lies, f) applying a second spacer material, which can be soaked with an incompletely reacted polyurethane and which takes the form of a desired second PU sublayer, and g) casting the second PU sublayer by saturating the second spacer material so that the first and second PU sublayers bond reactively and enclose the reinforcement where first and second two PU sublayers come into contact during hardening of the polyurethane of the superposed PU sublayer.

The first and second PU sublayers bond with the aid of the primer applied between the PU sublayers.

Use of the primer according to the third embodiment is particularly attractive when the casting resin reacts rapidly to completion or when work on the reinforcement takes a relatively long time such that the first or lower PU sublayer has hardened or substantially hardened. The second PU sublayer binds with the aid of the primer while the second or superposed PU layer completes its reaction.

The polyurethane for the sublayers surrounding the reinforcement can contain aromatic or aliphatic isocyanates, particularly a polyurethane based on aliphatic isocyanates, and more particularly HDI. At least 50% by weight, and particularly at least 70% by weight, of the isocyanates of the PU casting resin should be aliphatic.

According to the invention, the socket or the mounting is constructed over the shape of the amputated stump in a plurality of steps. The general method includes constructing a prefabricated positive model (e.g. plaster of Paris model) of the amputated stump.

Optionally, additional sublayers may surround the actual PU sublayers surrounding the reinforcement. Various coatings and additional protective outward-facing sublayers can be used, e.g. textile coverings and the like. If additional sublayers are at the interior of the socket, these additional sublayers would first be applied to the male mold. Otherwise, step a) is carried out first after a separation means or a separator foil has been applied to the male mold.

As in step a), a spacer material which takes the form of the desired limb-proximal PU sublayer and which can be saturated with the incompletely reacted polyurethane (i.e. with the castable PU composition provided, which is also termed casting resin) is applied at the spatial position of the PU sublayer below the reinforcement. The shape of the subsequent PU sublayer is modeled or prescribed via this spacer material. As a function of the shape of the subsequent mounting and of the region of the limb, the spacer material assumes the shape of a sublayer (layer), sleeve or cup.

In another embodiment of the invention, during the casting procedure a separator foil is placed around the spacer material and peeled away after the casting resin has hardened or after dimensional stability of the sublayer has been achieved. This type of separator foil is not necessary if the spacer material is saturated by pouring material from the outside without any dripping of the casting composition. If appropriate, the flow of the casting composition into the space between the male mold or lower layers and the foil is promoted by suction to remove the displaced air. Casting processes of this type are known to persons skilled in the art.

In step b) the reinforcement is placed around the first spacer material, i.e. over the subsequent first PU sublayer.

The reinforcement may be composed of a hard polymer, i.e. generally a material whose stiffness is higher than that of the polyurethane provided. Fiber-reinforced plastics are particularly suitable. According to an embodiment of the invention, the reinforcement is a reinforced polyacrylate sublayer cast or molded above the first PU sublayer and windowed (i.e. subjected to a cutout process) after hardening. The production of a polyacrylate reinforcement of this type is known to persons skilled in the art. The sublayer is first cast or laminated in the form of a hard shell over the underlying PU layer, removed after hardening, and windowed at the points which are intended to be less stiff within the socket. However, other methods of producing the grid-like reinforcement are contemplated. By way of example, fillets of a separator foil composed of a suitable material having sufficient stiffness in the hardened state can be injected onto the lower PU sublayer and metallic splints could likewise be included, e.g. adhesive-bonded to a textile layer which has the shape of a grid, etc. The windowed polyacrylate sublayer can include carbon-fiber reinforcement by pouring acrylic resin onto carbon-fiber mats or carbon-fiber bandages.

After the reinforcement has been removed in step c), a first polyurethane sublayer is cast in step d) by saturating the spacer material or by placing a female mold around the spacer material, removing the spacer material and casting a polyurethane casting composition for an unreinforced sublayer of a single material into the space between the female mold and the substrate of the layer. A corresponding process has been described by way of example in EP 650 708 for the casting of a socket lining.

At least one layer of the spacer material is applied. The spacer material is a textile material such as a knitted material. This material may be filled with the casting composition to give a laminate.

In particular, the textile material can take the form of a stocking or sock, and in particular, a plurality of overlapping stockings or socks. An elastic knitted material is particularly advantageous. It is also possible to use bandages.

As an alternative, the spacer material can be composed of a porous sleeve and in particular, composed of a polyurethane foam. This type of open-cell porous material can also be filled with the PU casting resin. Other spacer materials may also be used.

Before complete reaction of the PU casting resin, any sublayer delimiting the casting or the separator foil is peeled away as soon as it is possible without causing any alteration or instability in the PU sublayer. In step e) the reinforcement previously removed is then again superposed on the polyurethane surface of the first polyurethane sublayer. At this point, the polyurethane sublayer is in a state of polymerization after dimensional stability has been achieved.

In step f), a further, second spacer material which can be saturated with the incompletely reacted polyurethane is applied, as previously done for the first PU sublayer, for a further PU sublayer surrounding the reinforcement.

In step g), the second PU layer is cast in a manner corresponding to that described for the first PU sublayer, i.e. by saturating the second spacer material in such a way that the two PU layers bond reactively where the two PU sublayers come into contact. The two PU layers bond during simultaneous hardening of the polyurethane of the two PU sublayers or alternatively during hardening of the superposed PU sublayer adjacent to the previously cast sublayer primer-treated in the PU-PU contact region.

The method for modeling the second spacer material sublayer is the same as that used previously for the first sublayer. The casting process also takes place in the manner previously described above for the first PU sublayer.

The effect of the process is that the two polyurethane sublayers, which enclose the reinforcement, behave like a coherent layer because the polyurethane is preferably subjected to a shared hardening process throughout.

When a primer is used, additional crosslinking simultaneously takes place between the PU layers during the polymerization reaction in at least the superposed PU sublayer by virtue of the primer. In the first case, the polymerization reaction does not merely penetrate one layer but extends into the two layers and also across the contact area. The reinforcement becomes completely enclosed and the windowed regions or the space within the meshes of a grid-like reinforcement or the interior of a frame are penetrated by a composition which undergoes uniform polymerization, and specifically either via a process of shared hardening of the two unhardened or incompletely hardened PU sublayers or alternatively or additionally via the hardening of the superposed PU sublayer on the previously cast lower PU sublayer which has been provided with primer. Separation of the layers originally regarded as individual layers in the structure of the socket is therefore prevented.

The polyurethane layers generally come into contact (contact area) at the edge of the socket. The reinforcement is thus generally shorter than the PU sublayers and does not extend to the edge of the socket. Another contact area is within all of the perforations of the reinforcement, as described above.

Further layers can be applied to the outside of the socket, for example, a decorative layer, a textile cover or the like.

According to an advantageous embodiment of the invention, a primer, adhesion promoter or adhesive, in particular those derived from a polymer solution, can be applied to the grid-like reinforcement. The primer, adhesion promoter or adhesive is applied generally all around the finished, removed reinforcement.

Primers of this type are known in principle to persons skilled in the art for bonding various plastics. These are often unfunctionalized or functionalized polymers in organic solvents which can swell or solvate the plastic to be treated. They can also be prepolymers in substance. Multicomponent systems are also possible and are mixed only shortly prior to use of the primer, adhesion promoter or adhesive.

If the reinforcement includes an acrylic resin, it is particularly advantageous to contact the acrylic resin reinforcement with a primer composed of a solvent for thermoplastic polyacrylates with or without polymer dissolved therein. Any of the organic solvents which dissolve, for example, (poly)methyl methacrylate are attractive as a solvent for the primer, particularly organic paint solvents, and more particularly 2-butanone (methyl ethyl ketone). The acrylic resin reinforcement is solvated by the butanone solvent and thus permits adhesion of the reinforcement to the adjacent sublayer by way of cold welding, promoted by the primer. Materials dissolved in the primer cannot only be the solvent, which can also be a solvent mixture, but also polymers.

Particularly suitable polymers are pressure-sensitive polymers, other adhesives or polymers such as those described herein. The solids content of this type of solution (polymer content) can amount from about 10 to about 50% by weight and more particularly from about 15 to about 25% by weight. Polymers having elements of the following groups or copolymers having elements of the following groups, either individually or in a mixture, are particularly suitable: methacrylate, acrylonitrile, vinyl chloride and vinyl acetate.

Regardless of the material of the reinforcement, it is possible as an optional measure to spread a primer on, or use a primer to treat, the first polyurethane sublayer, as described in more detail above, and specifically at least at the positions at which the two polyurethane sublayers come into contact around the reinforcement located between these sublayers, or alternatively over the entire surface. It is preferable that this primer is applied to improve bonding of the two PU sublayers outside the area with which the reinforcement is in contact and at least in the edge region of the first PU sublayer, i.e. at the edge of the socket or of the orthosis. By way of example, this can take place immediately after superposition of the reinforcement.

This type of primer which is effective between two PU sublayers can preferably be a solution of a reactive PU component, particularly an isocyanate-containing solution. In particular, substances of the following group, individually or in a mixture: MDI, 1,1-methylenebisisocyanatobenzene and 2,2,2,4-methylenediphenyl diisocyanate. Particularly suitable solvents are individual solvents or mixtures of hydrocarbons, inclusive of aromatic hydrocarbons. Particularly preference is given to the individual solvent or a solvent mixture composed of at least two constituents of the following group: xylene, naphtha petroleum, trimethylbenzene and ethylbenzene.

The invention also encompasses in general terms a mounting which is attachable to a human body and which includes, in its core region, a grid- or frame-like reinforcement whose stiffness is higher relative to its immediate surroundings, where a uniformly fully reacted region composed of a casting resin whose stiffness is lower relative to the reinforcement surrounds the reinforcement with penetration of its perforations.

The casting resin is a polyurethane-based material, particularly a polyurethane-based material based on aliphatic or predominantly aliphatic isocyanate. The PU-based material can in particular be a laminate composed of the PU and of a textile material, particularly a knitted material. The mounting is a prosthesis socket or an orthosis part.

A process for casting a prosthesis socket 10 is illustrated in FIGS. 1a, 1b, 1c, 1d and 1e. FIGS. 1a-1e show cross-sectional views of the structure of prosthesis socket 10 in various stages of processing.

FIG. 1a shows a first process stage in casting the prosthesis socket 10. A spacer material 31 forms a first sublayer surrounding a positive cast replica of an amputated stump 11. A first separator foil 21 is positioned on the positive cast replica 11 and is surrounded by a plurality of layers of elastic knitted stocking material as first spacer material 31.

Figure 1B:
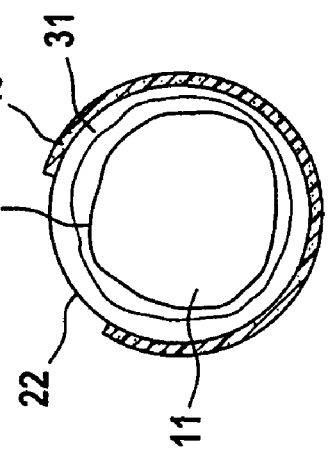
FIG. 1b is a cross-sectional view of the prosthesis socket during a second process stage.

As can be seen in FIG. 1b, in a second process stage, the positive cast replica 11 is surrounded with the first separator foil 21 and the spacer material 31 is covered by a second separator foil 22, on which a reinforcement 40 composed of carbon mats and acrylic resin was produced. The hardened reinforcement 40 extends around the second separator foil 22 as a shell and is subjected to usual mechanical operations (i.e., windowed), producing a reinforcement frame.

Figure 1C:
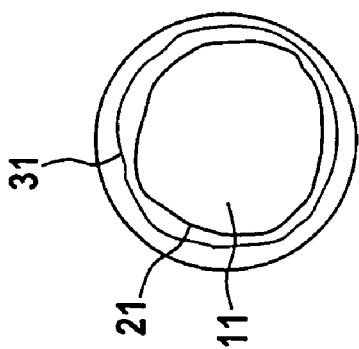
FIG. 1c is a cross-sectional view of the prosthesis socket during a third process stage.

FIG. 1c illustrates a third process stage and shows a cast limb-proximal PU sublayer 32 positioned below the reinforcement 40. The cast limb-proximal PU sublayer 32 is also defined as a lower, first, or inner PU sublayer. The cast limb-proximal PU sublayer 32 includes the thoroughly saturated first spacer material 31. The second separator foil 22 has also been removed. After the polyurethane has solidified to the extent that it has sufficient dimensional stability but has not yet hardened, the windowed reinforcement 40, on which primer may have been applied, is superposed.

Figure 1D:
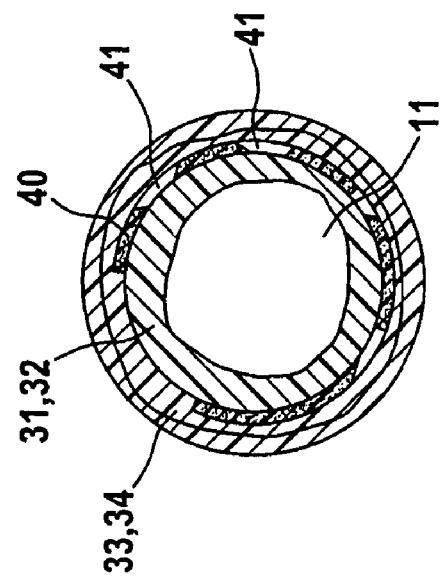
FIG. 1d is a cross-sectional view of the prosthesis socket during a fourth process stage.

FIG. 1d shows the reinforcement 40 and the window regions 41. The spacer layer 33 for a second PU sublayer 34 is now applied by again using elastic-knitted stocking material to cover the limb-proximal PU sublayer 32 and the reinforcement 40 in the shape of a grid. The second PU sublayer 34 is also defined as a superposed or outer PU sublayer.

Figure 1E:
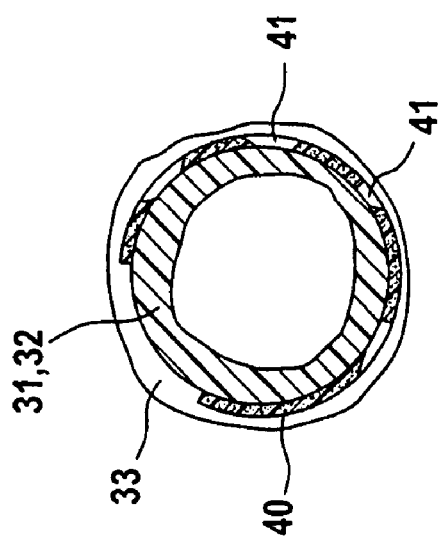
FIG. 1e is a cross-sectional view of the prosthesis socket during a fifth process stage.

Finally, FIG. 1e shows the cast second PU layer 34 which includes the spacer material 33 and which extends externally around the reinforcement. The PU sublayers layers 32 and 34 are in mutual contact around the reinforcement 40 and in the window regions 41. The two PU sublayers 32 and 34 can now undergo a shared hardening process and can bond.

Although no additional layers, such as coverings, or valves, spigots, etc are shown, these features may can be attached by any methods known in the art.

Figure 2B:
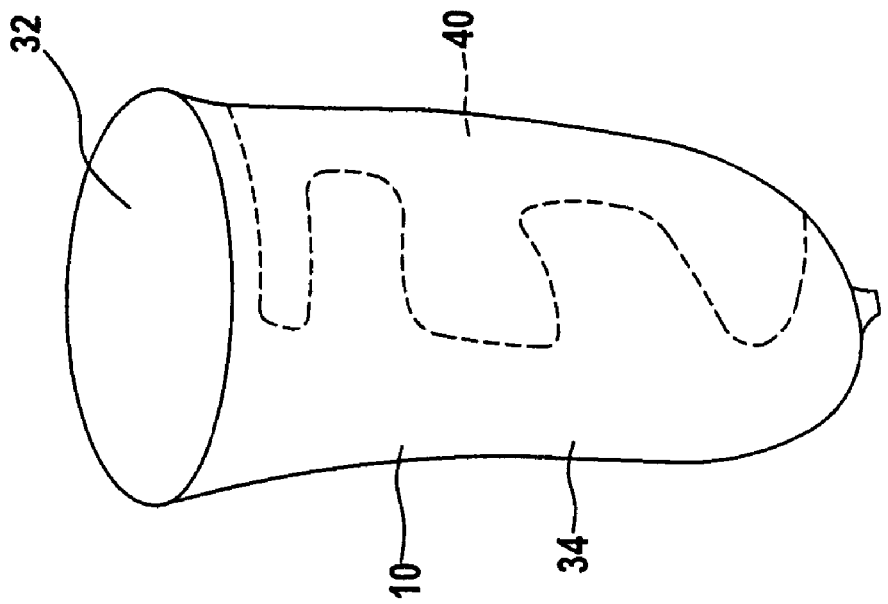
FIG. 2b is a side view of a second embodiment of the prosthesis socket.
Figure 2A:
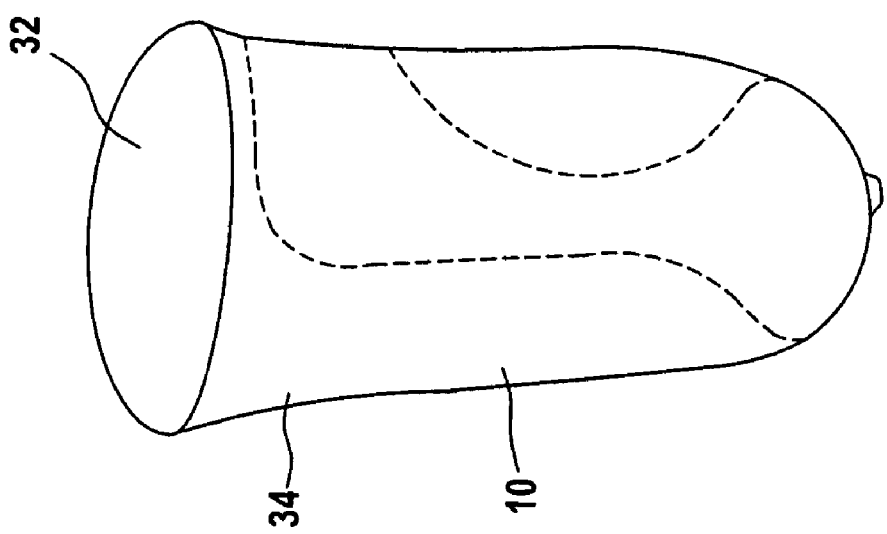
FIG. 2a is a side view of a first embodiment of the prosthesis socket.

FIGS. 2a and 2b show side views of a first embodiment and a second embodiment, respectively, of prosthesis sockets 10. The first and second embodiments differ only in the shape of the reinforcement 40. As can be seen, very different shapes can be selected and realized by the process. The PU sublayers 32 and 34 bond wherever no reinforcement is present between them.

EXAMPLES

Example 1

Materials

1. Polyurethane
   HDI-based multi-component system

2. Spacer material elastic, knitted polyamide stocking materials

3. Reinforcement
   carbon-reinforced polyacrylate (e.g. Bayer or Rohm Chemie)
   Separator foils composed of PVA Process A positive cast replica of an amputated stump is produced by any method known in the art. In addition, a rod can optionally be incorporated as a grip rod for easier handling. A separator foil was first superposed on the positive cast replica. The first spacer material for the first PU sublayer was then applied to the separator foil by applying and molding stocking materials in a plurality of layers. Unlike in known casting processes, the spacer material was not yet saturated with casting resin but was instead covered by a piece of foil. The reinforcement frame was produced thereon by covering the reinforcement region with carbon mats and saturating the reinforcement region with acrylic resin. The reinforcement was allowed to harden and then removed. The upper separator foil was then peeled away. The desired mechanical operations and windowing were carried out on the reinforcement, followed by casting of the PU layer located under the reinforcement. After the polyurethane solidified to the extent that it had sufficient dimensional stability but had not yet hardened, the windowed reinforcement was swiftly superposed, the spacer Layer for the next PU sublayer was applied (as described previously above for the first layer) and the PU layer extending around the outside of the reinforcement was cast. The two PU layers then underwent a shared hardening process and bonded. Elements such as valves, spigots, pendulum suspension, etc. are attached by any methods known in the art.

Example 2

A positive cast replica was produced and the process for casting the mounting took place as in Example 1, but additionally with primer for a polyacrylate reinforcement. The acrylic resin of the reinforcement was cured by a free-radical mechanism from a mixture composed of methyl methacrylate and prepolymerized PMMA with benzoyl peroxide (50% strength). The windowed reinforcement was in the completely hardened state throughout.

The entire surface of the reinforcement was treated with a primer composed of polyvinyl- chloride- and/or polyvinyl acetate-containing solution with 2-butanone as solvent. The solution included an epoxidized vinyl chloride-vinyl acetate copolymer.

Before the reinforcement was superposed on the lower PU sublayer, the primer first underwent initial physical drying so that the solvent evaporated to some extent.

Example 3

A positive cast replica was produced and the process for casting the mounting took place as in Example 1, with the addition of a primer between the two PU sublayers.

Immediately before the reinforcement was again superposed, having now been windowed, the first PU sublayer, produced via saturation of the spacer material after removal of the reinforcement, was spread with a primer which was composed of one of the following solutions, which can also be used in various mixtures with one another:

1) MDI (diphenylmethane 4,4'-diisocyanate) in a mixture composed of xylene, naphtha petroleum, trimethylbenzene, ethylbenzene, in equal parts;

2) 1,1-methylenebisisocyanatobenzene in a mixture composed of xylene, naphtha petroleum, trimethylbenzene, ethylbenzene, in equal parts:

3) 2,2,2,4-methylenediphenyl diisocyanate in a mixture composed of xylene, naphtha petroleum, trimethylbenzene, ethylbenzene, in equal parts.

The windowed reinforcement was then superposed and the PU sublayer over the reinforcement is produced.

Example 4

A positive cast replica was produced and the process for casting the mounting took place as in Example 2. After superposition of the reinforcement as provided in Example 2 with primer, the remaining free area of the first PU sublayer was spread as in Example 3 with a primer. The further processing took place as in Example 1.

The invention claimed is:

1. A process for casting a mounting attachable to a human body and which takes the form of a prosthesis socket or orthosis having a grid or frame-shaped reinforcement at its core region and having a lower polyurethane sublayer, a reinforcement in the core region and a superposed polyurethane sublayer, the process comprising:
   a. providing a first spacer material in spatial relation to the lower polyurethane sublayer;
   b. forming the reinforcement on the first spacer material;
   c. removing the reinforcement from the first spacer material;
   d. casting the lower polyurethane sublayer by saturating the first spacer material with an incompletely reacted polyurethane material;
   e. superimposing the reinforcement on a surface of the lower polyurethane sublayer after the lower polyurethane sublayer becomes dimensionally stable;
   f. applying a second spacer material; and
   g. casting the superposed polyurethane sublayer by saturating the second spacer material with an incompletely reacted polyurethane material wherein the lower and superposed polyurethane sublayers come into contact and wherein both sublayers bond reactively and enclose the reinforcement.

2. The process of claim 1, and further comprising applying a primer between the lower and superposed polyurethane sublayers to aid in bonding the lower and superposed polyurethane sublayers during hardening of the superposed polyurethane layer.

3. The process of claim 1, wherein the lower and superposed polyurethane sublayers bond reactively with aid of a simultaneous shared hardening process of the lower and superposed polyurethane sublayers.

4. The process of claim 1, wherein the lower and superposed polyurethane sublayers surrounding the reinforcement is a polyurethane based on aliphatic isocyanates.

5. The process of claim 4, wherein the polyurethane is based on HDI.

6. The process of claim 1, wherein the reinforcement is a reinforced polyacrylate sublayer cast or molded above the first polyurethane sublayer and windowed after hardening.

7. The process of claim 6, wherein the windowed polyacrylate sublayer has carbon-fiber reinforcement.

8. The process of claim 1, wherein casting the lower polyurethane sublayer comprises placing a separator foil around the first spacer material, saturating the first spacer material, and peeling away the separator foil after the polyurethane resin hardens or after achieving dimensional stability of the lower polyurethane sublayer, and wherein casting the superposed polyurethane sublayer comprises placing a separator foil around the second spacer material, saturating the second spacer material, and peeling away the separator foil after the polyurethane resin hardens or after achieving dimensional stability of the superposed polyurethane sublayer.

9. The process of claim 1, and further comprising applying at least one layer of the first spacer material and the second spacer material, and wherein the first and second spacer materials comprises a textile material or knitted material.

10. The process of claim 9, wherein the textile material takes the form of a stocking or sock, and wherein one or more layers of the textile material is overlapped.

11. The process of claim 1, wherein the first spacer material and second spacer material comprises a porous sleeve.

12. The process of claim 1, wherein the lower polyurethane sublayer is constructed on a cast replica of a limb part or stump.

13. The process of claim 12, wherein the lower polyurethane sublayer is constructed directly on the cast replica, on a separator foil or by a means of separation.

14. The process of claim 1, and further comprising applying a primer, adhesion promoter or adhesive to the reinforcement, to at least one of the lower and superposed polyurethane sublayers or to both the reinforcement and to at least one of the polyurethane sublayers.

15. A process for casting a mounting attachable to a human body and which takes the form of a prosthesis socket or orthosis having a grid or frame shaped reinforcement at its core region, the process comprising:
   a) providing a first spacer material in spatial relation to the a first polyurethane sublayer;
   b) producing the reinforcement on the first spacer material;
   c) removing the reinforcement;
   d) casting the first polyurethane sublayer by saturating the first spacer material with an incompletely reacted polyurethane material;
   e) superimposing the reinforcement on a free polyurethane surface of the first polyurethane sublayer prior to complete reaction of the polyurethane;
   f) applying a second spacer material; and
   g) casting a second polyurethane sublayer by saturating the second spacer material with an incompletely reacted polyurethane material so that the first and second polyurethane sublayers bond reactively and enclose the reinforcement where the first and second polyurethane sublayers come into contact.

16. The process of claim 15, wherein the polyurethane sublayers surrounding the reinforcement comprise a polyurethane based on aliphatic isocyanates.

17. The process of claim 16, wherein the polyurethane sublayers comprise a polyurethane based on HDI.

18. The process of claim 15, wherein the reinforcement is a reinforced polyacrylate sublayer cast or molded above the first polyurethane sublayer and windowed after hardening.

19. The process of claim 18, wherein the windowed polyacrylate sublayer has carbon-fiber reinforcement.

20. The process of claim 15, wherein casting the polyurethane sublayers comprises placing a separator foil around the spacer material, saturating the spacer material, and peeling away the separator foil after hardening of the casting resin or after achieving dimensional stability of the polyurethane sublayer.

21. The process of claim 15, and further comprising applying at least one layer of the first and second spacer materials, wherein each of the spacer materials is a textile material or knitted material.

22. The process of claim 21, wherein the textile material takes the form of a stocking or sock, and wherein one or more layers of the textile material is overlapped.

23. The process of claim 15, wherein each of the spacer material is composed of a porous sleeve.

24. The process of claim 15, and further comprising constructing the first polyurethane sublayer on a cast replica of a limb part or stump by mounting directly on the cast replica, on a separator foil or by a separating means.

25. The process of claim 15, and further comprising applying a primer, adhesion promoter or adhesive derived from a polymer solution to the reinforcement.

26. The process of claim 15, and further comprising applying an isocyanate-containing primer, adhesion promoter or adhesive at least to the first polyurethane sublayer.

27. A process for casting a prosthesis socket or orthosis having an inner polyurethane sublayer, an outer polyurethane sublayer and a grid or frame shaped reinforcement positioned between the inner and outer polyurethane sublayers, the process comprising:
   a) providing a first spacer material in spatial relation to the inner polyurethane sublayer;
   b) producing the reinforcement on the first spacer material;
   c) removing the reinforcement;
   d) casting the inner polyurethane sublayer by saturating the first spacer material with an incompletely reacted polyurethane material;
   e) superimposing the reinforcement on a polyurethane surface of the inner polyurethane sublayer in a state of polymerization after achievement of dimensional stability;
   f) applying a primer at least on an edge region of the inner polyurethane sublayer and outside an area on which the reinforcement lies;
   g) applying a second spacer material; and
   h) casting the outer polyurethane sublayer by saturating the second spacer material with an incompletely reacted polyurethane material;
   i) wherein the primer aids the reactive bonding between the inner and outer polyurethane sublayers such that the inner and outer polyurethane sublayers enclose the reinforcement where the inner and outer polyurethane sublayers come into contact during hardening of the polyurethane of the superposed polyurethane sublayer.

28. The process of claim 27, wherein the polyurethane sublayers comprise a polyurethane derived from aliphatic isocyanates.

29. The process of claim 28, wherein the polyurethane sublayers comprise a polyurethane derived from HDI.

30. The process of claim 27, wherein the reinforcement is a reinforced polyacrylate and is windowed after hardening.

31. The process of claim 30, wherein the windowed polyacrylate sublayer has carbon-fiber reinforcement.

32. The process of claim 27, wherein casting the polyurethane sublayers comprises placing a separator foil around the respective spacer material, saturating the spacer material with a polyurethane resin and peeling away the separator foil after the polyurethane resin hardens or after achievement of dimensional stability of the respective polyurethane sublayer.

33. The process of claim 27 and further comprising applying at least one layer of the first spacer material and second spacer material and wherein each of the spacer materials is a textile material or knitted material.

34. The process of claim 33, wherein the textile material takes the form of a stocking or sock, and wherein one or more sublayers of the textile material is overlapped.

35. The process of claim 27, wherein each of the spacer materials is composed of a porous sleeve.

36. The process of claim 27, wherein the inner polyurethane sublayer is constructed on a positive cast replica of a limb part or stump to be provided with the mounting directly on the cast replica, by way of a separator foil or by separating means.

37. The process of claim 27, and further comprising applying a primer, adhesion promoter or adhesive derived from a polymer solution to the reinforcement.

38. The process of claim 27, and further comprising applying an isocyanate-containing primer, adhesion promoter or adhesive to the inner polyurethane sublayer.

* * * * *